United States Patent
Liu et al.

(10) Patent No.: US 11,733,237 B2
(45) Date of Patent: Aug. 22, 2023

(54) METHODS AND REAGENTS FOR DETERMINING IMMUNOGLOBULIN GAMMA (IGG) ANTIBODY ISOTYPE CONCENTRATION FROM BIOLOGICAL SAMPLES

(71) Applicant: Sartorius BioAnalytical Instruments, Inc., Bohemia, NY (US)

(72) Inventors: Zhaoping Liu, Albuquerque, NM (US); Thomas Duensing, Albuquerque, NM (US)

(73) Assignee: Sartorius BioAnalytical Instruments, Inc., Bohemia, NY (US)

( * ) Notice: Subject to any disclaimer, the term of this patent is extended or adjusted under 35 U.S.C. 154(b) by 760 days.

(21) Appl. No.: 15/824,905

(22) Filed: Nov. 28, 2017

(65) Prior Publication Data

US 2018/0203002 A1    Jul. 19, 2018

Related U.S. Application Data (60) Provisional application No. 62/447,772, filed on Jan. 18, 2017.

(51) Int. Cl.
  *G01N 33/53* (2006.01)
  *G01N 33/542* (2006.01)
  *G01N 33/68* (2006.01)
  *G01N 33/543* (2006.01)

(52) U.S. Cl.
  CPC ..... *G01N 33/542* (2013.01); *G01N 33/54326* (2013.01); *G01N 33/686* (2013.01); *G01N 33/6854* (2013.01)

(58) Field of Classification Search
  CPC ............... G01N 33/542; G01N 33/686; G01N 33/54326; G01N 33/6854; G01N 15/14; G01N 2470/00; G01N 2470/04; G01N 2470/06; G01N 2470/10; G01N 2470/12
  See application file for complete search history.

(56) References Cited

U.S. PATENT DOCUMENTS

| | | |
|---|---|---|
| 2004/0253634 A1 | 12/2004 | Wang |
| 2005/0032138 A1 | 2/2005 | Lathrop et al. |
| 2005/0153381 A1 | 7/2005 | Marusich et al. |
| 2005/0255491 A1 | 11/2005 | Lee et al. |
| 2006/0216766 A1 | 9/2006 | Rye |
| 2013/0165335 A1 | 6/2013 | Lea |
| 2014/0031249 A1 | 1/2014 | Lea |
| 2014/0141995 A1 | 5/2014 | Crisanti et al. |

FOREIGN PATENT DOCUMENTS

| | | | |
|---|---|---|---|
| CN | 101871937 | 10/2010 | |
| CN | 103197077 | 7/2013 | |
| CN | 105717033 | 6/2016 | |
| JP | H 04363663 A | 12/1992 | |
| JP | 09-501505 | 10/1997 | |
| WO | WO 01/57527 A2 | 8/2001 | |
| WO | WO2007067680 * | 6/2007 | ........... G01N 33/543 |
| WO | WO 2009/082798 A1 | 7/2009 | |
| WO | WO 2014/096389 A1 | 6/2014 | |
| WO | WO 2014/151763 A1 | 9/2014 | |

OTHER PUBLICATIONS

Molecular Probes Bead Kit (2014; retrieved from https://www.thermofisher.com/document-connect/document-connect.html?url=https%3A%2F%2Fassets.thermofisher.com%2FTFS-Assets%2FLSG%2Fmanuals%2Fabc_total_ab_compensation_bead_kit_man.pdf&title=QWJDlFRvdGFslEFudGlib2R5lENvbXBlbnNhdGlvbiBCZWFkIEtpdA==).*

Kimpegowda et al.(2005;retrieved https://core.ac.uk/download/pdf/5164221.pdf).*

Technical Guide for ELISA KPL (2005; retrieved from URL http://www.kpl.com/docs/techdocs/KPL%20ELISA%20Technical%20Guide.pdf).*

Maranon, et al., "A competitive enzyme immunoassay Subclass for the determination of total IgG-subclass levels in human serum. Comparison with single radial immunodiffusion," Journal of Immunoassay, May 1994, 15(2): 147-156.

Aucoutrier, et al., "Distribution of IgG subclass levels in normal adult sera as determined by a competitive enzyme immunoassay using monoclonal antibodies," Diagnostic Immunology, 1985, 3(4): 191-196.

Anderson, et al., "Detection of immunoglobulin isotypes from dried blood spots," Journal of Immunological Methods, Dec. 2013, 404:24-32.

International Search Report for PCT/US2017/063516, dated Apr. 16, 2018.

Duensing et al., "Antibody screening using high-throughput flow cytometry" Cold Spring Harbor Protocol 2018 (1):7-12 (Jan. 2018).

Duensing et al., "A novel clone ranking and selection assay that combines all the relevant insight need to choose the most optimal clones in a single experiment" The Journal of Immunology 198(Suppl. 1):4 pages (May 2017).

Gray et al., "Secretion capture and report web: use of affinity derivatized agarose microdroplets for the secretion of hybridoma cells" J of Immunological Methods, 182(2):155-63 (Jun. 1995).

Intellicyt: Cy-Clone PLUS Intellicyt, 3 pages Feb. 2017.

(Continued)

*Primary Examiner* — Carmencita M Belei
(74) *Attorney, Agent, or Firm* — McDonnell Boehnen Hulbert & Berghoff LLP

(57) ABSTRACT

Disclosed herein are methods and reagents for determining immunoglobulin gamma (IgG) antibody isotype concentration from biological samples, and for analyzing a plurality of cell samples for IgG antibody production.

11 Claims, 2 Drawing Sheets

(56) References Cited

OTHER PUBLICATIONS

Kenney et al., "Production of monoclonal antibodies using a secretion capture report web" Biotechnololgy 13(8):787-90 (Aug. 1995).
Weaver et al., "Gel microdrop technology for rapid isolation of rare high producer cells" Nature Medicine 3(5):585-85 (May 1997).
Goldman et al., "Multiplexed Toxin Analysis Using Four Colors of Quantum Dot Fluororeagents" Analytical Chemistry 76(3):684-88 (Feb. 2004).
Intellicyt—"A novel multiplexed screening assay for assessing productivity of antibody secreting lines: Simultaneous measurement of secreted protein and viable cell count" pp. 1-4, Sep. 2011.
Bio-Plex Pro—Instruction Manual—Immunoglobulin Isotyping Assay—pp. 1-35, 2006.
Campbell et al., "Development of a highly-sensitive multi-plex assay using monoclonal antibodies for the simultaneous measurement of kappa and lambda immunoglobulin free light chains in serum and urine." J Immunol Methods, . May 31, 2013;391(1-2):1-13.
Ketsuyu Kensayo Tesutosuteronkito Shimensu Imuraizu Totaru Tesutosuteron II, 2000, 16 pages, Apr. 2013. Submitted with English translation.

\* cited by examiner

METHODS AND REAGENTS FOR DETERMINING IMMUNOGLOBULIN GAMMA (IGG) ANTIBODY ISOTYPE CONCENTRATION FROM BIOLOGICAL SAMPLES

CROSS-REFERENCE

This application claims priority to U.S. Provisional Patent Application Ser. No. 62/447,772 filed Jan. 18, 2017, incorporated by reference herein in its entirety.

BACKGROUND

Protein biologics are the fastest growing therapeutic modality. These drugs are usually protein (i.e., IgG) molecules that are administered to patients and alter a specific physiological process involved in disease. Commercial manufacturing processes for protein biologics is a long, expensive and arduous process. This is because most protein biologics are manufactured within living cell lines such as bacteria, yeast, insect and mammalian cells. These cell lines are typically genetically engineered to produce and secrete the protein biologic of interest into the extracellular milieu (the cell culture supernatant). Once the biologic is secreted, it is harvested and purified for commercial use. Because of the expensive nature of this process, it is desirable to engineer the production cell lines so that they produce very high levels of the protein of interest.

SUMMARY OF THE INVENTION

In one aspect are provided methods for determining immunoglobulin gamma (IgG) antibody isotype concentration from biological samples, comprising:

(a) in plurality of wells in a microtiter plate, incubating biological samples containing IgG antibodies with detection reagents, wherein the detection reagents comprise one or more detectably labeled target IgG protein isotypes, or fragments thereof, wherein the incubating occurs for a time and under conditions to promote even mixing of the detectably labeled target IgG proteins or fragments thereof with the IgG antibodies thereof to produce IgG antibody-target IgG protein mixtures in each well of the plurality of wells (b) incubating the IgG antibody-target IgG protein mixture in each well of the plurality of wells with one or more IgG isotype-specific populations of capture reagents, wherein each IgG isotype-specific population of capture reagents comprises binding molecules that selectively bind to a different specific IgG protein isotype, wherein the binding molecules in each IgG isotype-specific population of capture reagents are bound to a surface, wherein the incubating is carried out for a time and under conditions to promote binding of the one or more detectably labeled target IgG proteins or fragments thereof and the IgG antibodies to the IgG isotype-specific population of capture reagents, to produce IgG isotype-specific binding complexes; and (c) detecting signal from the IgG isotype-specific binding complexes to determine the concentration of one or more IgG antibody isotypes present in the biological sample, wherein the amount of an IgG antibody isotype present in the biological sample is inversely proportional to the detected signal from the relevant IgG isotype-specific binding complex.

In one embodiment, the method further comprises (d) incubating serial dilutions of a control sample, wherein each dilution of the serial dilutions of the control sample is present in a separate well of a microtiter plate, with the detection reagents to generate control mixtures, wherein the control sample comprises one or more different unlabeled IgG protein isotypes, or fragments thereof, that correspond to the one or more different, detectably labeled target IgG protein isotypes or fragments thereof in the detection reagents, wherein the incubation occurs for a time and under conditions to promote mixing of the unlabeled IgG protein isotypes in the control sample and the one or more different, detectably labeled target IgG protein isotypes, or fragments thereof;

(e) incubating the control mixtures with the one or more IgG isotype-specific populations of capture reagents, wherein the incubating is carried out for a time and under conditions to promote competitive binding of the one or more detectably labeled target IgG protein isotypes or fragments thereof and the one or more different unlabeled IgG protein isotype or fragments thereof to the one or more IgG isotype-specific population of capture beads, to produce control IgG isotype-specific binding complexes; and (f) generating a standard curve for each IgG protein isotype by analysis of the signal from the IgG isotype-specific binding complexes, wherein the concentration of the one or more IgG antibody isotypes in each biological sample is measured by reference to the standard curve for each IgG protein isotype.

In another aspect are provided methods for determining immunoglobulin gamma (IgG) isotype antibody concentration from biological samples, comprising:

(a) in plurality of wells in a microtiter plate, incubating a plurality of biological samples expressing IgG antibodies with one or more IgG isotype-specific populations of capture reagents, wherein each IgG isotype-specific population of capture reagents comprises binding molecules that selectively bind to a different specific IgG protein isotype, wherein the binding molecules in each IgG isotype-specific population of capture reagents are bound to a surface; wherein the incubating is carried out for a time and under conditions to promote binding of the IgG antibodies to the IgG isotype-specific capture reagents to produce IgG antibody-IgG isotype-specific capture reagent complexes;

(b) incubating the IgG antibody-IgG isotype-specific capture reagent complexes with detection reagents, wherein the detection reagents comprise one or more detectably labeled target IgG protein isotypes, or fragments thereof, wherein the incubation occurs for a time and under conditions to promote binding of the detectably labeled target IgG protein isotypes, or fragments thereof, to unoccupied sites on the IgG isotype-specific capture reagent complexes to produce detectably labeled target IgG protein-IgG antibody-IgG isotype-specific capture reagent complexes; and (c) detecting signal from the detectably labeled target IgG protein on the detectably labeled target IgG protein-IgG antibody-IgG isotype-specific capture reagent complexes to determine the concentration of one or more IgG antibody isotypes, wherein the amount of an IgG antibody isotype protein present in the biological sample is inversely proportional to the detected signal.

In one embodiment, the methods further comprise (d) incubating serial dilutions of a control sample, wherein each dilution of the serial dilutions of the control sample is present in a separate well of a microtiter plate, with one or more IgG isotype-specific populations of capture reagents, to generate a control mixture, wherein the control sample comprises one or more different unlabeled IgG protein isotypes, or fragments thereof, that correspond to the one or more different, detectably labeled target IgG protein isotypes or fragments thereof in the detection reagents, wherein the incubating is carried out for a time and under conditions to promote binding of the one or more different unlabeled IgG protein isotypes to the IgG isotype-specific capture reagents produce control complexes;

(e) incubating the control complexes with the detection reagents, wherein the incubating is carried out for a time and under conditions to promote binding of one or more detectably labeled IgG protein isotypes or fragments thereof, to unoccupied sites on the IgG isotype-specific capture reagents; and (f) generating a standard curve for each IgG protein isotype by analysis of the signal from the detectably labeled IgG isotype bound to the IgG isotype-specific population of capture reagents, wherein the concentration of one or more IgG isotypes in each biological sample is measured by reference to the standard curve for each IgG protein isotype.

In various embodiments of either aspect, the detection reagents comprise a defined ratio of two, three, four or more different, detectably labeled target IgG protein isotypes, or fragments thereof, and the concentration of two, three, or four or more IgG antibody isotypes is determined in each biological sample.

In a further embodiment, the detection reagent may further comprise a detectable cell viability marker, and wherein the methods further comprise measuring cell viability and/or cell number in each biological sample. In another embodiment, the surface to which the binding molecules are bound may comprise a bead. In one embodiment each population of capture reagents is separately distinguishable. In a further embodiment, the binding molecules comprise antibodies, affimers aptamers, and/or Fc receptors. In another embodiment, the methods further comprise determining the total IgG antibody concentration in each biological sample. In a further embodiment, the biological samples comprise cell samples. In one embodiment, the biological sample is an undiluted sample. In another embodiment, the methods do not include any wash steps.

In one embodiment, the biological samples comprises mouse B cells or mouse cell hybridoma supernatant with or without cells, wherein the different IgG isotypes are selected from the group consisting of mouse IgG1, IgG2a, IgG2b, and IgG3. In another embodiment, the biological samples comprise human cells, wherein the different IgG isotypes are selected from the group consisting of human IgG1, IgG2, IgG3, and IgG4. In a further embodiment, the biological samples comprise rat cells, wherein the different IgG isotypes are selected from the group consisting of rat IgG1, IgG2a, IgG2b, IgG2c. In other embodiments, the biological samples comprise:

(i) rabbit cells or sheep cells, wherein the different IgG isotypes are selected from the group consisting of rabbit or sheep IgG;

(ii) goat cells, pig cells, or bovine cells, wherein the different IgG isotypes are selected from the group consisting of goat, pig, or bovine IgG1 and IgG2;

(iii) horse cells, wherein the different IgG isotypes are selected from the group consisting of horse IgGa, IgGb, IgGt; or (iv) monkey cells, wherein the different IgG isotypes are selected from the group consisting of monkey IgG1, IgG2, IgG3, IgG4.

In another aspect are provided kits comprising:

(a) a detection reagent, comprising a defined ratio of two, three, four, or more different, detectably labeled target IgG protein isotypes, or antigenic fragments thereof; and (b) two, three, four, or more populations of capture reagents, wherein each population of capture reagents comprises binding molecules that selectively bind to a different IgG antibody isotype, wherein the binding molecules in each population of capture reagents are bound to a surface.

In one embodiment, the surface comprises a bead. In another embodiment, each population of capture reagents is separately distinguishable. In a further embodiment, the binding molecules comprise antibodies. In another embodiment, the kits further comprise a control sample comprising a defined ratio of two or more different unlabeled IgG protein isotypes, or antigenic fragments thereof, that correspond to the two or more different, detectably labeled target IgG protein isotypes, or antigenic fragments thereof in the detection reagents. In one embodiment, the control sample comprising a defined ratio of three or more or four or more different unlabeled IgG protein isotypes, or antigenic fragments thereof, that correspond to the three or more or four or more different, detectably labeled target IgG protein isotypes, or antigenic fragments thereof in the detection reagents.

In one embodiment, the detection reagent, comprising a defined ratio of 2, 3, or 4 different, detectably labeled target mouse IgG protein isotypes selected from the group consisting of gG1, IgG2a, IgG2b, and IgG3, or antigenic fragments thereof; and the capture reagent comprises 2, 3, or 4 populations of capture reagents, wherein each population of capture reagents comprises binding molecules that selectively bind to a different mouse IgG antibody isotype selected from the group consisting of IgG1, IgG2a, IgG2b, and IgG3. In another embodiment, the detection reagent, comprising a defined ratio of 2, 3, or 4 different, detectably labeled target human IgG protein isotypes selected from the group consisting of IgG1, IgG2, IgG3, and IgG4, or antigenic fragments thereof; and the capture reagent comprises 2, 3, or 4 populations of capture reagents, wherein each population of capture reagents comprises binding molecules that selectively bind to a different human IgG antibody isotype selected from the group consisting of IgG1, IgG2, IgG3, and IgG4. In a still further embodiment, the detection reagent comprises a defined ratio of 2, 3, or 4 different, detectably labeled target rat IgG protein isotypes selected from the group consisting of IgG1, IgG2a, IgG2b, IgG2c or fragments thereof; and the capture reagent comprises 2, 3, or 4 populations of capture reagents, wherein each population of capture reagents comprises binding molecules that selectively bind to a different rat IgG antibody isotype selected from the group consisting of IgG1, IgG2a, IgG2b, IgG2c. In various other embodiments, (A) the detection reagent comprises a defined ratio of:
  (i) 2 different, detectably labeled target goat, pig, or bovine IgG protein isotypes selected from the group consisting of IgG1, IgG2 or fragments thereof;
  (ii) 2 or 3 different, detectably labeled target horse IgG protein isotypes selected from the group consisting of IgGa, IgGb, IgGt or fragments thereof, or
  (iii) 2, 3, or 4 different, detectably labeled target monkey IgG protein isotypes selected from the group consisting of IgG1, IgG2, IgG3, IgG4 or fragments thereof; and (B) the capture reagent comprises
  (i) 2 populations of capture reagents, wherein each population of capture reagents comprises binding molecules that selectively bind to a different target goat, pig, or bovine IgG protein isotype selected from the group consisting of IgG1, IgG2 or fragments thereof;
  (ii) 2 or 3 populations of capture reagents, wherein each population of capture reagents comprises binding molecules that selectively bind to a different horse IgG protein isotype selected from the group consisting of IgGa, IgGb, IgGt or fragments thereof; or (iii) 2, 3, or 4 populations of capture reagents, wherein each population of capture reagents comprises binding molecules that selectively bind to a different monkey IgG protein isotype selected from the group consisting of IgG1, IgG2, IgG3, IgG4 or fragments thereof.

In another aspect are provided methods for analyzing a plurality of cell samples for immunoglobulin gamma (IgG) antibody production, the method comprising:

(a) transferring a plurality of cell samples to an assay plate having a plurality of sample wells, wherein each sample well contains a cell sample that is an undiluted cell culture expressing a target IgG antibody and mixing the plurality of cell samples with analysis reagents to generate a plurality of analysis mixtures, wherein the analysis reagents comprise:
  (i) a capture bead, wherein the capture bead binds to IgG antibody; and
  (ii) a first detection molecule comprising (A) a control IgG antibody or fragment thereof, and (B) a first detectable moiety;

(b) incubating the plurality of analysis mixtures for a time and under conditions to promote binding of the target IgG antibody and the first detection molecule to the capture bead; and (c) determining the target IgG antibody concentration in each analysis mixture of the plurality of analysis mixtures by flow cytometry analysis.

In one embodiment, the cell culture is propagated from a single clone. In another embodiment, the capture bead is covalently linked with Protein G or Protein A. In a further embodiment, the capture bead is a magnetic bead or an agarose bead. In another embodiment, the assay plate contains lyophilized analysis reagents before the plurality of samples are transferred. In one embodiment, mixing the analysis reagents with the plurality of samples comprises adding the analysis reagents to the cell sample in the wells. In another embodiment, the assay plate is centrifuged before reading the plurality of analysis mixtures in the assay plate in a flow cytometer. In a further embodiment, the mixing comprises simultaneously mixing the plurality of cell samples and all of analysis reagents, wherein the first detection molecule competes with the target IgG antibody for binding to the capture bead; and wherein the amount of the first detection molecule bound to the capture bead in each analysis mixture provides a measure of the target IgG antibody concentration in a given analysis mixture. In another embodiment, the mixing comprises stepwise addition of the capture beads and the first detection molecule, wherein the stepwise addition comprises:

first mixing the plurality of cell samples with the capture beads for a time and under conditions to promote binding of the target IgG antibody to the capture beads to generate a plurality of first mixtures, and then adding the first detection molecules to the plurality of first mixtures for a time and under conditions to promote binding of the first detection molecules to the capture beads to generate the plurality of analysis mixtures;

wherein the amount of the first detection molecule bound to the capture bead in each analysis mixture provides a measure of the target IgG antibody concentration in a given analysis mixture.

In another aspect are provided methods for analyzing a plurality of cell samples for immunoglobulin gamma (IgG) antibody production, the method comprising:

(a) transferring a plurality of cell samples to an assay plate having a plurality of sample wells, wherein each sample well contains a cell sample that is an undiluted cell culture expressing a target IgG antibody and mixing the plurality of cell samples with analysis reagents to generate a plurality of analysis mixtures, wherein the analysis reagents comprise:
  (i) a capture bead, wherein the capture bead binds to IgG antibody; and
  (ii) a first detection molecule comprising a first detectable moiety;

(b) incubating the plurality of analysis mixtures for a time and under conditions to promote binding of the target IgG antibody and the first detection molecule to the capture bead; and (c) determining the target IgG antibody concentration in each analysis mixture of the plurality of analysis mixtures by flow cytometry analysis.

In one embodiment, the first detection molecule lacks immunoglobulin light chains and is capable of binding to the capture bead. In another embodiment, the method further comprises contacting the plurality of analysis mixtures with a second detection molecule for a time and under conditions to promote binding of the second detection molecule to the target IgG antibody bound to the capture bead;

wherein the second detection molecule comprises a detectably labeled anti-IgG light chain antibody that is optically distinguishable from the first detection molecule; and wherein the amount of the second detection molecule bound to the target IgG antibody in each analysis mixture provides a measure of intact target IgG antibody concentration in a given analysis mixture.

In another embodiment, the plurality of analysis mixtures are centrifuged and subjected to a wash step before the labeled anti-light chain antibody is added. In a further embodiment, the analysis reagents further comprises one or more of a cell viability dye, a cell surface biomarker, or a marker of apoptosis. In various embodiments, the methods further comprise determining one or more of:
  (i) a number of cells in each analysis mixture;
  (ii) a percentage of viable cells in each analysis mixture;
  (ii) a concentration of target IgG antibody per cell in each analysis mixture; and/or
  (iii) a concentration of target IgG antibody per viable cell in each analysis mixture.

In another aspect are provided kits comprising:
(a) an assay plate, and
(b) analysis reagents, wherein the analysis reagents comprise:
  (i) a capture bead, wherein the capture bead binds to IgG antibody; and
  (ii) a first detection molecule comprising a first detectable moiety.

In one embodiment, the first detection molecule comprises a control IgG antibody or fragment thereof. In another embodiment the kit further comprises a detectably labeled anti-light chain antibody that is optically distinguishable from the first detection molecule. In a further embodiment, the analysis reagents further comprises one or more of a cell viability dye, a cell surface biomarker, or a marker of apoptosis. In another embodiment, the capture bead is covalently linked with Protein G or Protein A. In a further embodiment, the capture bead is a magnetic bead or an agarose bead. In another embodiment, the assay plate contains lyophilized analysis reagents.

DETAILED DESCRIPTION

All references cited are herein incorporated by reference in their entirety.

As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In a first aspect are provided methods for determining immunoglobulin gamma (IgG) antibody isotype concentration from biological samples, comprising:

(a) in plurality of wells in a microtiter plate, incubating biological samples containing IgG antibodies with detection reagents, wherein the detection reagents comprise one or more detectably labeled target IgG protein isotypes, or fragments thereof, wherein the incubating occurs for a time and under conditions to promote even mixing of the detectably labeled target IgG proteins or fragments thereof with the IgG antibodies thereof to produce IgG antibody-target IgG protein mixtures in each well of the plurality of wells (b) incubating the IgG antibody-target IgG protein mixture in each well of the plurality of wells with one or more IgG isotype-specific populations of capture reagents, wherein each IgG isotype-specific population of capture reagents comprises binding molecules that selectively bind to a different specific IgG protein isotype, wherein the binding molecules in each IgG isotype-specific population of capture reagents are bound to a surface, wherein the incubating is carried out for a time and under conditions to promote binding of the one or more detectably labeled target IgG proteins or fragments thereof and the IgG antibodies to the IgG isotype-specific population of capture reagents, to produce IgG isotype-specific binding complexes; and (c) detecting signal from the IgG isotype-specific binding complexes to determine the concentration of one or more IgG antibody isotypes present in the biological sample, wherein the amount of an IgG antibody isotype present in the biological sample is inversely proportional to the detected signal from the relevant IgG isotype-specific binding complex.

The methods permit determining the concentration of one or more IgG antibody isotypes present in the biological sample based on the inverse relationship of the IgG antibody isotype present in the biological sample is inversely proportional to the detected signal from the relevant IgG isotype-specific binding complex.

Any suitable biological sample that contains IgG antibodies can be used, including but not limited to isolated IgG antibody-secreting cells, populations of IgG antibody-secreting cells, supernatants of such cells, cell extracts thereof, serum, serum extracts, biological fluids (including but not limited to blood), and biological fluid extracts (including but not limited to blood extracts). In non-limiting embodiments, the biological sample may comprise antibody-secreting B cells, hybridoma cells, supernatants thereof (i.e., cell culture media in which the cells or hybridomas have been cultured, with or without the cell component), or cell extracts thereof. In certain embodiments, the biological sample comprises cells propagated from a single clone. In other embodiments, the biological sample comprises an undefined cell population. In one embodiment, the biological sample is an undiluted sample, such as an undiluted sample from cell/hybridoma culture. The methods of the invention permit quantitation of IgG antibody isotypes without dilution of the cell/hybridoma culture samples, which is not possible using previous antibody concentration detection techniques and greatly simplifies the assay workflow by removing the intermediate sample dilution step which may require the subjective guess of the dilution factor.

The biological sample may be of any origin, including but not limited to human, rodent (i.e., mouse, rat, hamster, etc.), rabbit, pig, goat, monkey, sheep, horse, bovine, etc.

As used herein, the IgG antibodies in the biological sample may be polyclonal or monoclonal antibodies. In a specific embodiment, the IgG antibodies in the biological sample are monoclonal antibodies, fragments thereof, or immunological binding equivalents thereof. Such antibodies include any type of antibody that a cell may express or be engineered to express, including but not limited to monoclonal antibodies (mAbs), humanized or chimeric antibodies, single chain antibodies (scFvs), Fab fragments, F(ab')$_2$ fragments, disulfide-linked Fvs (sdFv) fragments, anti-idiotypic (anti-Id) antibodies, intra-bodies, synthetic antibodies, epitope-binding fragments of any of the above, and fusion protein that includes a region equivalent to the IgG Fc region.

The detection reagents comprise one or more detectably labeled target IgG protein isotypes, or fragments thereof that retain the ability to bind to the corresponding IgG antibody isotype. In various embodiments, the detection reagents comprise 2, 3, 4, 5, or more detectably labeled target IgG protein isotypes, or fragments thereof. Such IgG proteins are commercially available from a number of vendors, including BD Biosciences, Sigma Chemical Company, Millipore, and ThermoFisher Scientific. Each target IgG protein isotype, or fragment thereof has the ability to bind to a specific IgG antibody isotype. In one non-limiting embodiment, the biological samples comprises mouse B cells or mouse cell hybridoma supernatant (with or without cells), and the different IgG isotypes are selected from the group consisting of mouse IgG1, IgG2a, IgG2b, and IgG3. In this embodiment, the detection reagent comprises 1, 2, 3, or 4 detectably labeled target IgG protein isotypes (i.e.: IgG1, IgG2a, IgG2b, and/or IgG3), or fragments thereof. In another non-limiting embodiment, the biological samples comprise human antibody-secreting cells, and the different IgG isotypes are selected from the group consisting of human IgG1, IgG2, IgG3, and IgG4. In this embodiment, the detection reagent comprises 1, 2, 3, or 4 detectably labeled target IgG protein isotypes or fragments thereof. In a further non-limiting embodiment, the biological samples comprise rat antibody-secreting cells, and the different IgG isotypes are selected from the group consisting of rat IgG1, IgG2a, IgG2b, IgG2c. In this embodiment, the detection reagent comprises 1, 2, 3, or 4 detectably labeled target IgG protein isotypes or fragments thereof. In various further embodiments, (i) the biological samples comprises rabbit or sheep antibody-secreting cells, and the only IgG isotypes are rabbit or sheep IgG;

(ii) the biological samples comprises goat, pig, or bovine antibody-secreting cells, and the different IgG isotypes are selected from the group consisting of goat, pig, or bovine IgG1 and IgG2. In this embodiment, the detection reagent comprises 1 or 2 detectably labeled target IgG protein isotypes or fragments thereof;

(iii) the biological sample comprises horse antibody-secreting cells, and the different IgG isotypes are selected from the group consisting of horse IgGa, IgGb, IgGt. In these embodiment, the detection reagent comprises 1, 2, or 3 detectably labeled target IgG protein isotypes or fragments thereof or (iv) the biological sample comprises antibody-secreting monkey cells, and the different IgG isotypes are selected from the group consisting of monkey IgG1, IgG2, IgG3, IgG4. In this embodiment, the detection reagent comprises 1, 2, 3, or 4 detectably labeled target IgG protein isotypes or fragments thereof.

In various embodiments the detection reagents comprise a defined ratio of 2, 3, 4 or more different, detectably labeled target IgG protein isotypes or fragments thereof. This embodiment permits more rapid quantification of the concentration of 2, 3, 4, or more IgG antibody isotypes in the biological sample. Any defined ratio of the detectably labeled target IgG protein isotypes or fragments thereof may be used, so long as the ratio is known. In one non-limiting embodiment, each detectably labeled target IgG protein isotype or fragment thereof is present in about the same concentration. In another non-limiting embodiment, each detectably labeled target IgG protein isotype or fragment thereof is present in about the same amount (i.e., about 1:1:1 when there are three different, detectably labeled target IgG protein isotypes or fragments thereof).

Any suitable concentration of target IgG protein isotypes or fragments thereof can be used in the assays. In one non-limiting embodiment, each target IgG protein isotype or fragment thereof in the detection reagent is present at between about 1 ng/ml to about 10 mg/ml. In various other embodiments, each target IgG protein isotype or fragment thereof in the detection reagent is present at between about 10 ng/ml to about 1 mg/ml, about 100 ng/ml to about 750 µg/ml, about 500 ng/ml to about 500 µg/ml, about 1 µg/ml to about 250 µg/ml, or at least 125 µg/ml.

Any suitable detectable label can be used, including but not limited to a fluorescent label, hapten, colorimetric label, various radioactive labels, enzymes, prosthetic groups, fluorescent markers, luminescent markers, bioluminescent markers, labeled particles such as silicon, glass, or metal particles; protein-protein binding pairs, protein-antibody binding pairs and the like. Examples of fluorescent labels include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, cyanines, dansyl chloride, phycocyanin, allophycocyanin (APC), brilliant violet dye, brilliant ultraviolet dye, and phycoerythrin. Examples of bioluminescent markers include, but are not limited to, luciferase (e.g., bacterial, firefly, click beetle and the like), luciferin, aequorin and the like. Examples of enzyme systems having visually detectable signals include, but are not limited to, galactosidases, glucorinidases, phosphatases, peroxidases, cholinesterases and the like. Detectable labels are commercially available from a variety of sources. In certain embodiments the detection label comprises a fluorophore or fluorescent protein. When the detection reagents comprise 2, 3, 4 or more different, detectably labeled target IgG protein isotypes or fragments thereof, each different population of detectably labeled target IgG protein isotypes or fragments thereof may have the same or a distinguishable label, depending on the intended detection assay.

In a further embodiment, the detection reagent further comprises a detectable cell viability marker, and the methods further comprise measuring cell viability and/or cell number in each biological sample. Any suitable cell viability marker can be used. A cell viability dye can allow for the detection non-viable cells in a sample. For example the cell viability dye can permanently label dead cells allowing them to be excluded from analysis even when the cell preparation is being analyzed by flow cytometry for intracellular targets (for example Fixable Viability Dye eFlour®, Propidium iodide (PI) is a membrane impermeant dye that is generally excluded from viable cells). A cell viability dye can also label live cells. For example, a non-fluorescent compound freely enters live cells and intracellular esterases convert it to a fluorescent dye. In such an example, the dye will not be retained in cells after fixation or permeabilization and therefore, is not useful for intracellular staining protocols. In some embodiments, the analysis reagents further comprises a cell surface biomarker or a marker of apoptosis. Those skilled in the art recognized that cell surface markers are proteins expressed on the surface of cells and can often conveniently serve as markers of specific cell types. For example, T cell and B cell surface markers identify their lineage and stage in the differentiation process.

The incubating occurs for a time and under conditions to promote even mixing of the detectably labeled target IgG proteins or fragments thereof with the IgG antibodies thereof to produce IgG antibody-target IgG protein mixtures in each well of the plurality of wells. Any suitable conditions to promote such even mixing may be used, and it is well within the level of those of skill in the art to determine such appropriate conditions as temperature, humidity levels, length of incubation, application of stirring or other mixing forces, medium to be used, etc.

The method comprises incubating the IgG antibody-target IgG protein mixture in each well of the plurality of wells with one or more IgG isotype-specific populations of capture reagents, wherein each IgG isotype-specific population of capture reagents comprises binding molecules that selectively bind to a different specific IgG protein isotype. Each population of capture reagent is specific for a different specific IgG protein isotype, and thus can be used to segregate the IgG antibody-target IgG protein mixture based on the IgG isotype. Any suitable binding molecules can be used that selectively bind to a specific IgG protein isotype. In various non-limiting embodiments, the binding molecules comprise antibodies, affimers aptamers, Fc receptors, or other protein/sugar/lipid or combination molecules. In one specific embodiment, the binding molecules comprise antibodies that selectively bind to an IgG protein isotype. Such IgG isotype selective antibodies are commercially available from a number of vendors, including BD Biosciences, Sigma Chemical Company, Millipore, and ThermoFisher Scientific.

The binding molecules in each IgG isotype-specific population of capture reagents are bound to a surface. Any suitable surface can be used, including but not limited to glass, cellulose, polyacrylamide, nylon, polystyrene, polyvinyl chloride, polypropylene supports, magnetic or paramagnetic beads, agarose beads, and filtration media such as NETS-activated Sepharose or CNBr-activated Sepharose. In one specific embodiment, the binding molecules in each IgG isotype-specific population of capture reagents are bound to a bead, such as a magnetic or paramagnetic bead. A magnetic or paramagnetic capture bead is typically about 1 mm in diameter or less, and is sufficiently small enough in order to prevent sedimentation or clogging. Suitable beads are known to those of skill in art and can be obtained from different sources (e.g., DYNABEADS MY-ONE™ beads from Invitrogen Dynal, Norway or Estapore from Merck, France). Beads can be pre-coupled or coated with binding molecules for passive or active coupling of antibodies or antigens. In other embodiments, the capture bead can be an agarose bead. Typically agarose beads are about 20 µm to 350 µm in diameter. In another specific embodiment, the binding molecules in each IgG isotype-specific population of capture reagents are present in a printed array in the wells of a micro-titer plate.

Any suitable density of capture reagents can be used in the assays. In one non-limiting embodiment, each population of capture reagents are present at a density of between about 0.01 million to about 100 million capture reagents per milliliter. In various further embodiments, each population of capture reagents are present at a density of between about 0.1 million to about 50 million, between about 0.25 million to about 25 million, between about 0.5 million to about 10 million capture, or between about 0.75 million to about 5 million capture reagents per milliliter.

The incubating is carried out for a time and under conditions to promote binding of the one or more detectably labeled target IgG proteins or fragments thereof and the IgG antibodies to the IgG isotype-specific population of capture reagents, to produce IgG isotype-specific binding complexes. Any suitable conditions to promote such even mixing may be used, and it is well within the level of those of skill in the art to determine such appropriate conditions as temperature, humidity levels, length of incubation, application of stirring or other mixing forces, medium to be used, etc.

Signal (i.e.: from the detectably labeled target IgG protein isotypes or fragments thereof) is detected from the IgG isotype-specific binding complexes to determine the concentration of one or more IgG antibody isotypes present in the biological sample. As this is a competition assay, the amount of an IgG antibody isotype present in the biological sample is inversely proportional to the detected signal from the relevant IgG isotype-specific binding complex. Any suitable technique for detecting signal from the IgG isotype-specific binding complexes can be used depending on the detectable label employed, including but not limited to enzyme-linked immunosorbent assays (ELISA), flow cytometry, plate reader, Meso Scale Discovery platform, and fluorescent microscopy. In one specific embodiment, the detection involves flow cytometry, by suspending IgG isotype-specific binding complexes in a stream of fluid and passing them by an electronic detection apparatus, allowing simultaneous multi-parametric analysis of the physical and chemical characteristics of up to tens of thousands of complexes per second.

In one embodiment, the methods further comprise generating a standard curve for each IgG protein isotype, wherein the concentration of the one or more IgG antibody isotypes in each biological sample is measured by reference to the standard curve for each IgG protein isotype. In one such embodiment, the method further comprises (d) incubating serial dilutions of a control sample, wherein each dilution of the serial dilutions of the control sample is present in a separate well of a microtiter plate, with the detection reagents to generate control mixtures, wherein the control sample comprises one or more different unlabeled IgG protein isotypes, or fragments thereof, that correspond to the one or more different, detectably labeled target IgG protein isotypes or fragments thereof in the detection reagents, wherein the incubation occurs for a time and under conditions to promote mixing of the unlabeled IgG protein isotypes in the control sample and the one or more different, detectably labeled target IgG protein isotypes, or fragments thereof;

(e) incubating the control mixtures with the one or more IgG isotype-specific populations of capture reagents, wherein the incubating is carried out for a time and under conditions to promote competitive binding of the one or more detectably labeled target IgG protein isotypes or fragments thereof and the one or more different unlabeled IgG protein isotype or fragments thereof to the one or more IgG isotype-specific population of capture beads, to produce control IgG isotype-specific binding complexes; and (f) generating a standard curve for each IgG protein isotype by analysis of the signal from the IgG isotype-specific binding complexes, wherein the concentration of the one or more IgG antibody isotypes in each biological sample is measured by reference to the standard curve for each IgG protein isotype.

In this embodiment, the one or more detectably labeled target IgG protein isotypes, or fragments thereof and the one or more different unlabeled IgG protein isotypes, or fragments thereof compete for binding to the IgG isotype-specific population of capture reagents. The amount of an IgG antibody isotype present in the biological sample is inversely proportional to the detected signal from the relevant IgG isotype-specific binding complex, and can be interpolated from IgG isotype-specific standard curve and be quantitated by the positive quantity above the baseline quantity calculated from a control well with a zero concentration of unlabeled IgG protein isotype or fragments thereof.

In a second aspect are provided methods for determining immunoglobulin gamma (IgG) isotype antibody concentration from biological samples, comprising:

(a) in plurality of wells in a microtiter plate, incubating a plurality of biological samples expressing IgG antibodies with one or more IgG isotype-specific populations of capture reagents, wherein each IgG isotype-specific population of capture reagents comprises binding molecules that selectively bind to a different specific IgG protein isotype, wherein the binding molecules in each IgG isotype-specific population of capture reagents are bound to a surface; wherein the incubating is carried out for a time and under conditions to promote binding of the IgG antibodies to the IgG isotype-specific capture reagents to produce IgG antibody-IgG isotype-specific capture reagent complexes;

(b) incubating the IgG antibody-IgG isotype-specific capture reagent complexes with detection reagents, wherein the detection reagents comprise one or more detectably labeled target IgG protein isotypes, or fragments thereof, wherein the incubation occurs for a time and under conditions to promote binding of the detectably labeled target IgG protein isotypes, or fragments thereof, to unoccupied sites on the IgG isotype-specific capture reagent complexes to produce detectably labeled target IgG protein-IgG antibody-IgG isotype-specific capture reagent complexes; and (c) detecting signal from the detectably labeled target IgG protein on the detectably labeled target IgG protein-IgG antibody-IgG isotype-specific capture reagent complexes to determine the concentration of one or more IgG antibody isotypes, wherein the amount of an IgG antibody isotype protein present in the biological sample is inversely proportional to the detected signal.

In this aspect, the methods follow a pre-incubation protocol.

For hybridoma culture, such as mouse hybridoma culture, the full competition assay protocol may be preferred. This protocol can handle quantitation of IgG range commonly seen in mouse hybridoma culture (1-50 ug/mL).

For B cell cultures, the pre-incubation assay protocol may be preferred. This protocol is an adjusted competition protocol. For low-level IgG sample, pre-incubation of the capture reagents and the biological sample before the addition of the detection/competition reagent may better detect the low level of IgG in the sample This protocol can handle better the quantitation of mouse IgG range commonly seen in, for example, mouse B cell culture (0.1-2 µg/mL).

All embodiments of the first aspect of the invention are suitable for use in the second aspect of the invention. In one embodiment, the methods further comprise generating a standard curve for each IgG protein isotype, wherein the concentration of the one or more IgG antibody isotypes in each biological sample is measured by reference to the standard curve for each IgG protein isotype. In one such embodiment, the method further comprises (d) incubating serial dilutions of a control sample, wherein each dilution of the serial dilutions of the control sample is present in a separate well of a microtiter plate, with one or more IgG isotype-specific populations of capture reagents, to generate a control mixture, wherein the control sample comprises one or more different unlabeled IgG protein isotypes, or fragments thereof, that correspond to the one or more different, detectably labeled target IgG protein isotypes or fragments thereof in the detection reagents, wherein the incubating is carried out for a time and under conditions to promote binding of the one or more different unlabeled IgG protein isotypes to the IgG isotype-specific capture reagents produce control complexes;

(e) incubating the control complexes with the detection reagents, wherein the incubating is carried out for a time and under conditions to promote binding of one or more detectably labeled IgG protein isotypes or fragments thereof, to unoccupied sites on the IgG isotype-specific capture reagents; and (f) generating a standard curve for each IgG protein isotype by analysis of the signal from the detectably labeled IgG isotype bound to the IgG isotype-specific population of capture reagents, wherein the concentration of one or more IgG isotypes in each biological sample is measured by reference to the standard curve for each IgG protein isotype.

In this embodiment, the one or more detectably labeled target IgG protein isotypes, or fragments thereof and the one or more different unlabeled IgG protein isotypes, or fragments thereof compete for binding to the IgG isotype-specific population of capture reagents. The amount of an IgG antibody isotype present in the biological sample is inversely proportional to the detected signal from the relevant IgG isotype-specific binding complex, and can be interpolated from IgG isotype-specific standard curve and be quantitated by the positive quantity above the baseline quantity calculated from a control well with a zero concentration of unlabeled IgG protein isotype or fragments thereof.

In one embodiment of the first or second aspects of the invention, the method further comprises determining the total IgG antibody concentration in each biological sample. Any suitable method for determining the total IgG antibody concentration can be used. In embodiments where the amount of each IgG isotype present in the biological sample is determined, this embodiment may simply require adding the amount of each individual IgG isotype concentration to arrive at the total IgG antibody concentration.

In another embodiment of the first or second aspects of the invention, the methods do not include any wash steps, which removes the labor-intensive handling time and improves the data integrity by decreasing the wash-related readout variation such as the counts of cells, beads or both.

In a third aspect, the disclosure provides a method for analyzing a plurality of cell samples for immunoglobulin gamma (IgG) antibody production, the method comprising: (a) transferring a plurality of cell samples to an assay plate having a plurality of sample wells, wherein each sample well contains a cell sample that is an undiluted cell culture expressing a target IgG antibody and mixing the plurality of cell samples with analysis reagents to generate a plurality of analysis mixtures, wherein the analysis reagents comprise: (i) a capture bead, wherein the capture bead binds to IgG antibody; and (ii) a first detection molecule comprising (A) a control IgG antibody or fragment thereof, and (B) a first detectable moiety; (b) incubating the plurality of analysis mixtures for a time and under conditions to promote binding of the target IgG antibody and the first detection molecule to the capture bead; and (c) determining the target IgG antibody concentration in each analysis mixture of the plurality of analysis mixtures by flow cytometry analysis. In some embodiments, the mixing of the analysis reagents with the plurality of samples comprises adding the analysis reagents to the cell sample in the wells. In other embodiments, the mixing comprises simultaneously mixing the plurality of cell samples and all of analysis reagents, wherein the first detection molecule competes with the target IgG antibody for binding to the capture bead; and wherein the amount of the first detection molecule bound to the capture bead in each analysis mixture provides a measure of the target IgG antibody concentration in a given analysis mixture. In yet another embodiment, the method comprises mixing comprises stepwise addition of the capture beads and the first detection molecule, wherein the stepwise addition comprises: first mixing the plurality of cell samples with the capture beads for a time and under conditions to promote binding of the target IgG antibody to the capture beads to generate a plurality of first mixtures, and then adding the first detection molecules to the plurality of first mixtures for a time and under conditions to promote binding of the first detection molecules to the capture beads to generate the plurality of analysis mixtures; wherein the amount of the first detection molecule bound to the capture bead in each analysis mixture provides a measure of the target IgG antibody concentration in a given analysis mixture.

In certain embodiments, the cell culture is propagated from a single clone. In other embodiments, the cell population is undefined. Typically, a gene of interest is introduced into a population of candidate producer cells. Chromosomal integration into host chromosomes is a rare event, thus stably-transfected cells usually have to be selected and cultured in various ways. For example, for the selection of stably-transfected cells, a selection marker is co-expressed with the gene of interest. A variety of systems for selecting transfected cells exists, including resistance to antibiotics such as neomycin phosphotransferase, conferring resistance to G418, dihydrofolate reductase (DHFR), or glutamine synthetase. Such systems are well known to those of skill in arts. After gene transfer, cells are cultivated in medium containing the selective agent. Only those cells which have integrated the plasmid survive, containing the drug resistant gene. The population of cells integrated with the gene of interest are diluted and distributed in wells of a multiwell "microtiter" plate so that only one cell is deposited in each well. The methods for doing this are well described in the art and know to a person of skill in the art. One cell per well is practically a difficult goal to achieve; although most wells contain one cell, there are many wells which have zero cells, and many wells which contain multiple cells. In general it is necessary to screen hundreds of thousands of wells to find a small number of cell lines that secrete high levels of protein.

As used in this third aspect, the term "capture bead" refers to any molecule that is capable of providing a support for binding to an IgG molecule or protein of interest. In certain embodiments, the capture bead is covalently linked with a molecule that specifically binds to an IgG molecule or protein of interest. For example, Protein G and Protein A selectively bind antibodies through the Fab and Fc regions. Protein G or Protein A or other immunoglobulin-binding bacterial proteins such as Protein A/G and Protein L can be used to bind/detect immunoglobulins. In other embodiments, the capture bead can be covalently linked with an antibody that specifically recognizes an IgG antibody or a molecule that is specifically bound by a target antibody. In some embodiments, the capture bead is a magnetic bead or an agarose bead. A magnetic or paramagnetic capture bead is typically about 1 mm in diameter or less, and is sufficiently small enough in order to prevent sedimentation or clogging. Suitable microbeads are known to those of skill in art and can be obtained from different sources (e.g., DYNA-BEADS MY-ONE™ beads from Invitrogen Dynal, Norway or Estapore from Merck, France). As noted above, beads can be pre-coupled (with a specific affinity reagent such as Protein G) or coated with different molecules for passive or active coupling of antibodies or antigens. In other embodiments, the capture bead can be an agarose bead. Typically agarose beads are about 350 µm to 20 µm in diameter.

As used in this third aspect, the term "detection molecule" refers to any molecule that allows for the detection of a target IgG molecule or protein of interest. In certain embodiments the detection molecule comprises a detectable moiety such as a fluorophore or fluorescent protein. A detectable moiety, can be used to label the detection molecule. A detectable moiety can include, for example, a fluorescent moiety, hapten, colorimetric moiety, various radioactive moieties, enzymes, prosthetic groups, fluorescent markers, luminescent markers, bioluminescent markers, metal particles, protein-protein binding pairs, protein-antibody binding pairs and the like. Examples of fluorescent moieties include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, cyanines, dansyl chloride, phycocyanin, phycoerythrin. Examples of bioluminescent markers include, but are not limited to, luciferase (e.g., bacterial, firefly, click beetle and the like), luciferin, aequorin and the like. Examples of enzyme systems having visually detectable signals include, but are not limited to, galactosidases, glucorinidases, phosphatases, peroxidases, cholinesterases and the like. Detectable moieties are commercially available from a variety of sources.

In certain embodiments, the assay plate contains lyophilized analysis reagents. Lyophilisation is the creation of a stable preparation of a substance by rapid freezing and dehydration of the frozen product under high vacuum. A lyophilized biological material should be both intact and active, and also has the advantages of rapid dissolution and ideally suited to laboratory process automation, as well as a long shelf-life at ambient temperature which is desirable for warehousing, transport and end-user storage of the product.

In a fourth aspect, the disclosure provides a method for analyzing a plurality of cell samples for immunoglobulin gamma (IgG) antibody production, the method comprising: (a) transferring a plurality of cell samples to an assay plate having a plurality of sample wells, wherein each sample well contains a cell sample that is an undiluted cell culture expressing a target IgG antibody and mixing the plurality of cell samples with analysis reagents to generate a plurality of analysis mixtures, wherein the analysis reagents comprise: (i) a capture bead, wherein the capture bead binds to IgG antibody; and (ii) a first detection molecule comprising a first detectable moiety; (b) incubating the plurality of analysis mixtures for a time and under conditions to promote binding of the target IgG antibody and the first detection molecule to the capture bead; and (c) determining the target IgG antibody concentration in each analysis mixture of the plurality of analysis mixtures by flow cytometry analysis. In certain embodiments, the first detection molecule lacks immunoglobulin light chains and is capable of binding to the capture bead. In some embodiments, the further comprises contacting the plurality of analysis mixtures with a second detection molecule for a time and under conditions to promote binding of the second detection molecule to the target IgG antibody bound to the capture bead; wherein the second detection molecule comprises a detectably labeled anti-IgG light chain antibody that is optically distinguishable from the first detection molecule; and wherein the amount of the second detection molecule bound to the target IgG antibody in each analysis mixture provides a measure of intact target IgG antibody concentration in a given analysis mixture. In certain embodiments, the plurality of analysis mixtures are centrifuged and subjected to a wash step before the labeled anti-light chain antibody is added.

In some embodiments, the analysis reagents further comprises one or more of a cell viability dye, a cell surface biomarker, or a marker of apoptosis. A cell viability dye can allow for the detection non-viable cells in a sample. For example the cell viability dye can permanently label dead cells allowing them to be excluded from analysis even when the cell preparation is being analyzed by flow cytometry for intracellular targets (for example Fixable Viability Dye eFlour®, Propidium iodide (PI) is a membrane impermeant dye that is generally excluded from viable cells). A cell viability dye can also label live cells. For example, a non-fluorescent compound freely enters live cells and intracellular esterases convert it to a fluorescent dye. In such an example, the dye will not be retained in cells after fixation or permeabilization and therefore, is not useful for intracellular staining protocols. In some embodiments, the analysis reagents further comprises a cell surface biomarker or a marker of apoptosis. Those skilled in the art recognized that cell surface markers are proteins expressed on the surface of cells and can often conveniently serve as markers of specific cell types. For example, T cell and B cell surface markers identify their lineage and stage in the differentiation process.

In certain embodiments, the method further comprises determining one or more of: a number of cells in each analysis mixture; a percentage of viable cells in each analysis mixture; a concentration of target IgG antibody per cell in each analysis mixture; and/or a concentration of target IgG antibody per viable cell in each analysis mixture. Is some embodiments, method can involve analysis software that plots concentration curves from known, user defined standards and uses those plots to determine the concentration of the secreted protein. In other embodiments, the number of producer cells present in the sample is determined. The software automatically determines the ratio of secreted protein to cell number, calculates the secreted protein concentration on a per cell basis, and identifies the wells which have the highest secreted protein per cell values. If the high throughput flow cytometry system is used in conjunction with a cell sorter, the software also controls the system to sort individual cells from high secretor wells to further purify a desired cell line.

In certain embodiments, the methods of the disclosed herein rely on flow cytometry analysis. In some embodiments the sample for flow cytometry is undiluted. In other examples, the sample is undiluted and does not undergo a wash step. In certain embodiments, the sample can be washed before analyzed with a glow cytometer. Flow cytometry can be employed in cell counting, cell sorting, biomarker detection and protein engineering, by suspending cells in a stream of fluid and passing them by an electronic detection apparatus.

In a fourth aspect, the invention provides kits comprising:

(a) a detection reagent, comprising a defined ratio of two or more different, detectably labeled target IgG protein isotypes, or antigenic fragments thereof; and (b) two or more populations of capture reagents, wherein each population of capture reagents comprises binding molecules that selectively bind to a different IgG antibody isotype, wherein the binding molecules in each population of capture reagents are bound to a surface.

The kits of this aspect can be used, for example, to carry out the methods described herein. All embodiments of the detection reagents and capture reagents of the first and second aspects can be used in kits of this aspect. The detection reagents comprise two or more different, detectably labeled target IgG protein isotypes, or fragments thereof that retain the ability to bind to the corresponding IgG antibody isotype. In various embodiments, the detection reagents comprise 3, 4, 5, or more detectably labeled target IgG protein isotypes, or fragments thereof. Each target IgG protein isotype, or fragment thereof has the ability to bind to a specific IgG antibody isotype. The detection reagent comprises a defined ratio of 2, 3, 4 or more different, detectably labeled target IgG protein isotypes or fragments thereof. This embodiment permits more rapid quantification of the concentration of 2, 3, 4, or more IgG antibody isotypes in a biological sample. Any defined ratio of the detectably labeled target IgG protein isotypes or fragments thereof may be used, so long as the ratio is known. In one non-limiting embodiment, each different, detectably labeled target IgG protein isotype or fragment thereof is present in about the same concentration. In another non-limiting embodiment, each detectably labeled target IgG protein isotype or fragment thereof is present in about the same amount (i.e., about 1:1:1 when there are three different, detectably labeled target IgG protein isotypes or fragments thereof). Any suitable concentration of target IgG protein isotypes or fragments thereof can be present in the detection reagent. In one non-limiting embodiment, each target IgG protein isotype or fragment thereof in the detection reagent is present at between about 1 ng/ml to about 10 mg/ml. In various other embodiments, each target IgG protein isotype or fragment thereof in the detection reagent is present at between about 10 ng/ml to about 1 mg/ml, about 100 ng/ml to about 750 µg/ml, about 500 ng/ml to about 500 µg/ml, about 1 µg/ml to about 250 µg/ml, or at least 125 µg/ml. Any suitable detectable label can be used, including but not limited to a fluorescent label, hapten, colorimetric label, various radioactive labels, enzymes, prosthetic groups, fluorescent markers, luminescent markers, bioluminescent markers, metal particles, protein-protein binding pairs, protein-antibody binding pairs and the like. Examples of fluorescent labels include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, cyanines, dansyl chloride, phycocyanin, phycoerythrin. Examples of bioluminescent markers include, but are not limited to, luciferase (e.g., bacterial, firefly, click beetle and the like), luciferin, aequorin and the like. Examples of enzyme systems having visually detectable signals include, but are not limited to, galactosidases, glucorinidases, phosphatases, peroxidases, cholinesterases and the like. Detectable labels are commercially available from a variety of sources. In certain embodiments the detection label comprises a fluorophore or fluorescent protein. Each different population of detectably labeled target IgG protein isotypes or fragments thereof may have the same or a distinguishable label, depending on the intended detection assay.

Each population of capture reagent is specific for a different specific IgG protein isotype, and thus can be used to segregate the IgG antibody-target IgG protein mixture based on the IgG isotype. Any suitable binding molecules can be used that selectively bind to a specific IgG protein isotype. In various non-limiting embodiments, the binding molecules comprise antibodies, affimers aptamers, Fc receptors, or other protein/sugar/lipid or combination molecules. In one specific embodiment, the binding molecules comprise antibodies that selectively bind to an IgG protein isotype.

The binding molecules in each IgG isotype-specific population of capture reagents are bound to a surface. Any suitable surface can be used, including but not limited to glass, cellulose, polyacrylamide, nylon, polystyrene, polyvinyl chloride, polypropylene supports, magnetic or paramagnetic beads, agarose beads, and filtration media such as NHS-activated Sepharose or CNBr-activated Sepharose. In one specific embodiment, the binding molecules in each IgG isotype-specific population of capture reagents are bound to a bead, such as a magnetic or paramagnetic bead. A magnetic or paramagnetic capture bead is typically about 1 mm in diameter or less, and is sufficiently small enough in order to prevent sedimentation or clogging. Suitable beads are known to those of skill in art and can be obtained from different sources (e.g., Dynabeads My-One™ from Invitrogen Dynal, Norway or Estapore from Merck, France). Beads can be pre-coupled or coated with binding molecules for passive or active coupling of antibodies or antigens. In other embodiments, the capture bead can be an agarose bead. Typically agarose beads are about 350 µm to 20 µm in diameter. In another specific embodiment, the binding molecules in each IgG isotype-specific population of capture reagents are present in a printed array in the wells of a micro-titer plate.

Any suitable density of capture reagents can be present in the kits. In one non-limiting embodiment, each population of capture reagents are present at a density of between about 0.01 million to about 100 million capture reagents per milliliter. In various further embodiments, each population of capture reagents are present at a density of between about 0.1 million to about 50 million, between about 0.25 million to about 25 million, between about 0.5 million to about 10 million capture, or between about 0.75 million to about 5 million capture reagents per milliliter. In one embodiment, the number of different, detectably labeled target IgG protein isotypes, or antigenic fragments thereof is the same as the number of capture reagents.

In one specific embodiment, the detection reagent comprises a defined ratio of 2, 3, or 4 different, detectably labeled target mouse IgG protein isotypes selected from the group consisting of gG1, IgG2a, IgG2b, and IgG3, or antigenic fragments thereof; and the capture reagent comprises 2, 3, or 4 populations of capture reagents, wherein each population of capture reagents comprises binding molecules that selectively bind to a different mouse IgG antibody isotype selected from the group consisting of IgG1, IgG2a, IgG2b, and IgG3.

In another specific embodiment, the detection reagent, comprises a defined ratio of 2, 3, or 4 different, detectably labeled target human IgG protein isotypes selected from the group consisting of gG1, IgG2, IgG3, and IgG4, or antigenic fragments thereof; and the capture reagent comprises 2, 3, or 4 populations of capture reagents, wherein each population of capture reagents comprises binding molecules that selectively bind to a different human IgG antibody isotype selected from the group consisting of IgG1, IgG2, IgG3, and IgG4.

In a further specific embodiment, the detection reagent comprises a defined ratio of 2, 3, or 4 different, detectably labeled target rat IgG protein isotypes selected from the group consisting of IgG1, IgG2a, IgG2b, IgG2c or fragments thereof; and the capture reagent comprises 2, 3, or 4 populations of capture reagents, wherein each population of capture reagents comprises binding molecules that selectively bind to a different rat IgG antibody isotype selected from the group consisting of IgG1, IgG2a, IgG2b, IgG2c.

In various further specific embodiments, (A) the detection reagent comprises a defined ratio of:
  (i) 2 different, detectably labeled target goat, pig, or bovine IgG protein isotypes selected from the group consisting of IgG1, IgG2 or fragments thereof;
  (ii) 2 or 3 different, detectably labeled target horse IgG protein isotypes selected from the group consisting of IgGa, IgGb, IgGt or fragments thereof; or
  (iii) 2, 3, or 4 different, detectably labeled target monkey IgG protein isotypes selected from the group consisting of IgG1, IgG2, IgG3, IgG4 or fragments thereof; and
(B) the capture reagent comprises
  (i) 2 populations of capture reagents, wherein each population of capture reagents comprises binding molecules that selectively bind to a different target goat, pig, or bovine IgG protein isotype selected from the group consisting of IgG1, IgG2 or fragments thereof;
  (ii) 2 or 3 populations of capture reagents, wherein each population of capture reagents comprises binding molecules that selectively bind to a different horse IgG protein isotype selected from the group consisting of IgGa, IgGb, IgGt or fragments thereof; or
  (iii) 2, 3, or 4 populations of capture reagents, wherein each population of capture reagents comprises binding molecules that selectively bind to a different monkey IgG protein isotype selected from the group consisting of IgG1, IgG2, IgG3, IgG4 or fragments thereof. In these embodiments, the capture reagents comprise binding molecules that bind to the species of IgG protein isotypes present in the detection reagents.

In another embodiment, the kits further comprise a control sample comprising a defined ratio of two or more (2, 3, 4, or more) different unlabeled IgG protein isotypes, or antigenic fragments thereof, that correspond to the two or more different, detectably labeled target IgG protein isotypes, or antigenic fragments thereof in the detection reagents. All embodiments of the control as disclosed in the first and second aspects can be used in the kits of this aspect.

The kits may further comprise any additional components as appropriate for an intended use. In one embodiment, the kits further comprise a detectable cell viability marker.

In a fifth aspect kits are provided, comprising:
  (a) an assay plate, and
  (b) analysis reagents, wherein the analysis reagents comprise:
    (i) a capture bead, wherein the capture bead binds to IgG antibody; and
    (ii) a first detection molecule comprising a first detectable moiety.

All embodiments disclosed in the third aspect can be used in this fifth aspect. In some embodiments, the first detection molecule comprises a control IgG antibody or fragment thereof. In other embodiments, the kit further comprises a detectably labeled anti-light chain antibody that is optically distinguishable from the first detection molecule. The kit can also further comprise one or more of a cell viability dye, a cell surface biomarker, or a marker of apoptosis. In one embodiment, the capture bead is covalently linked with Protein G or Protein A. In another embodiment, the capture bead is a magnetic bead or an agarose bead. In certain aspects, the kit comprises an assay plate containing lyophilized analysis reagents.

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

Example 1

Exemplary Reagent Preparation:
  1) Detection Reagent Mixture Preparation: Into a same tube/reservoir, add and mix fluorescein isocyothianate (FITC)-mouse IgG1, FITC-mouse IgG2a, FITC-mouse IgG2b, and FITC-mouse IgG3 and a red fluorescent cell membrane integrity dye into enough volume of 0.1% bovine serum albumin (BSA) in phosphate buffer saline (PBS). The final FITC-mouse IgG concentration may be 125 µg/mL for each isotype (IgG1, IgG2a, IgG2b, and IgG3) in the mixture. The final red fluorescent FL4 cell membrane integrity dye (IntelliCyt Corporation) in the mixture may be 1:200 diluted in the tube/reservoir.

2) Mouse IgG Standard Mixture Preparation: Prepare a vial of pre-mixed mouse IgG standard stock: Into a same vial, add and mix unlabeled mouse IgG1, IgG2a, IgG2b and IgG3 proteins. Each isotype may have, for example, 200 ug/mL concentration in the mixture. A serial titration of the pre-mixed mouse IgG may be performed with the fresh cell culture media (the same media being used in the culture plate or flask where the biological samples come from). These serially diluted standards may be used later in the assay setup to generate 4 standard curves (1 standard curve for each mouse IgG isotype).

3) Capture Reagent Mixture Preparation: Into a same tube/reservoir, add and mix mouse IgG1 capture bead, mouse IgG2a capture bead, mouse IgG2b capture bead, and mouse IgG3 capture beads into enough volume of 0.1% BSA in PBS. The final density of mouse IgG capture bead is 1 million per mL for each isotype (IgG1, IgG2a, IgG2b, and IgG3) capture bead.

A user may now follow, for example, either the full competition protocol or the pre-incubation protocol to run the mouse IgG quantitation/isotyping assay.

Mouse I2G Quantitation/Isotyping Assay (Full Competition Protocol)

Assay Setup for Full Competition Protocol:

This assay may use a no-wash workflow and provide results in terms of IgG concentration (e.g., µg/mL). It involves preparing a serial dilution of a reference protein mixture to generate 4 standard curves that are used to determine the concentration for 4 mouse IgG isotypes. The FITC detection signal on capture beads has an inverse relationship with mouse IgG concentration. 4 capture beads may be used in the assay with each bead specific for a single mouse IgG isotype. Total mouse IgG concentration may be calculated in each well by FORECYT™ (Intellicyt) software by adding up 4 mouse IgG isotype concentrations. Cell number and cell viability may also be analyzed if samples have cells in addition to mouse IgG supernatant.

In one exemplary protocol:
1. Add Detection Reagent Mixture (Mouse FITC-IgG and FL4 Membrane Integrity Dye), 5 µL/well of a microtiter plate;
2. Add IgG Sample/IgG Standard, 20 µL/well; Quick Spin (500 g, 5 seconds). Mix (2,000 rpm, 20 seconds).
3. Add Prepared 4-plex Capture Beads, 5 µL/well; Quick Spin (500 g, 5 seconds). Mix (2,000 rpm, 20 seconds). RT 60 mins.

The plate is now ready for signal detection, such as by sampling on an IQUE™ Screener flow cytometry platform.

Pre-Incubation Protocol Mouse IgG Quantitation/Isotyping Assay:

Assay Setup for Pre-Incubation Protocol

This assay may use a no-wash workflow and provides results in terms of IgG concentration (e.g., µg/mL). It may involve preparing a serial dilution of a reference protein mixture to generate 4 standard curves that are used to determine the concentration for 4 mouse IgG isotypes. The FITC detection signal on capture beads has an inverse relationship with mouse IgG concentration. 4 capture beads may be used in the assay with each bead specific for a single mouse IgG isotype. Total mouse IgG concentration may be calculated in each well, for example by FORECYT™ software, by adding up 4 mouse IgG isotype concentrations. Cell number and cell viability may also be analyzed if samples have cells in addition to mouse IgG supernatant.

In one exemplary protocol:
1. Add Prepared 4-plex Capture Beads, 5 µL/well;
2. Add IgG Sample/IgG Standard, 20 µL/well; Quick Spin (500 g, 5 seconds). Mix (2,000 rpm, 20 seconds). RT 30 mins.
3. Add Detection Reagent Mixture (Mouse FITC-IgG and FL4 Membrane Integrity Dye), 5 µL/well; Quick Spin (500 g, 5 seconds). Mix (2,000 rpm, 20 seconds). RT 60 mins without light.

The plate is now ready for signal detection, such as by sampling on an IQUE™ Screener flow cytometry platform.

Multiplexed 4 capture beads with one capture bead type to specifically capture a specific mouse IgG isotype will solve the inconsistent quantitation in traditional singleplex capture beads coated with general anti-mouse IgG antibody. 4 different mouse IgG isotypes have slight different protein structure which caused slight different binding affinity to the general anti-mouse IgG coated on beads. In a mouse hybridoma or B cell culture screening plate, different wells may have one of the 4 isotypes. If singleplex anti-mouse IgG capture beads were used to capture mouse IgG in each well of the plate, the same amount of mouse IgG but with different isotype in different wells may general different binding signal on beads, due to IgG isotype-dependent binding affinity difference, and the quantitation based on standard curve with a purified mouse IgG as standard (a natural mixture of 4 isotypes) will extrapolate different mouse IgG quantity. This will introduce imprecise quantity. A multiplexed assay with 4 different capture beads (one for each isotype) will solve this issue. For example, if A1 well in the microtiter plate has mouse IgG1, it will only be captured on mouse IgG1 capture beads in the mixed 4 capture beads. The fluorescent signal will be extrapolated to mouse IgG1 quantity by using the mouse IgG1 standard curve. If A2 well has mouse IgG2a, it will only be captured on mouse IgG2a capture beads in the mixed 4 capture beads, and the fluorescent signal on mouse IgG2a capture beads will be extrapolated to mouse IgG2a quantity by using the mouse IgG2a standard curve.

Figure 1:
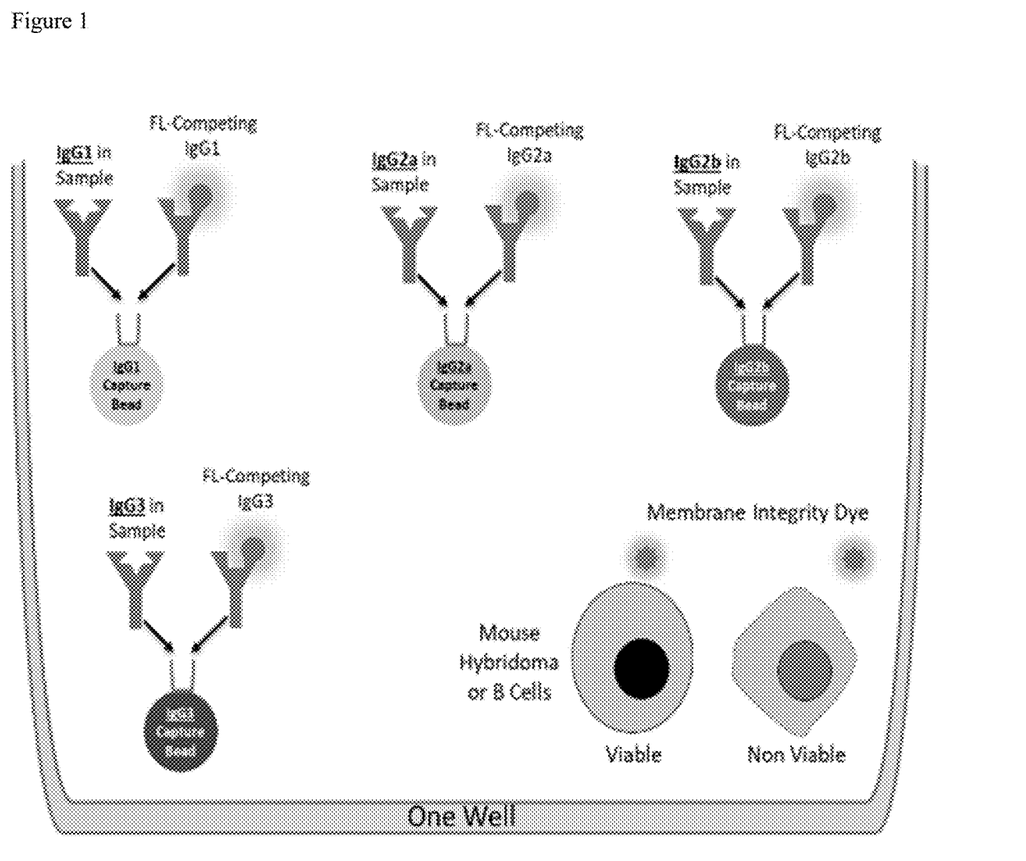
FIG. 1 is a diagram of multiplexed competition assay format with 4 capture beads to capture 4 different IgG isotypes.

Here we have established a multiplexed competition assay format with 4 capture beads to capture 4 different isotypes, and with 4 FITC-mouse IgG isotypes in the reaction (see FIG. 1). When the unknown isotype sample with or without cells is added into the reaction at the correct sequence, unknown and unlabeled mouse IgG isotype will compete one of the 4 FITC-mouse IgG isotype to only one of the 4 capture beads. It seems there is no any assay like this in measuring mouse IgG isotype and quantity. The assay does not need wash and dilution and can measure mouse IgG quantity/isotype from hybridoma supernatant which normally has mouse IgG concentration 1-50 ug/mL.

The assays may also allow users to measure the cell count and cell viability in the same multiplex assay. A user can either use the sample supernatant or the sample with cells inside. For the latter, the cell count and cell viability, and as well as the multiplexed beads, will be measured simultaneously in the high throughput flow cytometry.

The assays can be expanded/modified to measure the same endpoints (IgG isotype, IgG quantity for each isotype, cell number and cell health) for different species in addition to mouse species by modifying the isotype-specific capture antibody on the capture beads and the detection reagents and standard proteins from mouse species to other species such as human or rat, etc.

Figure 2:
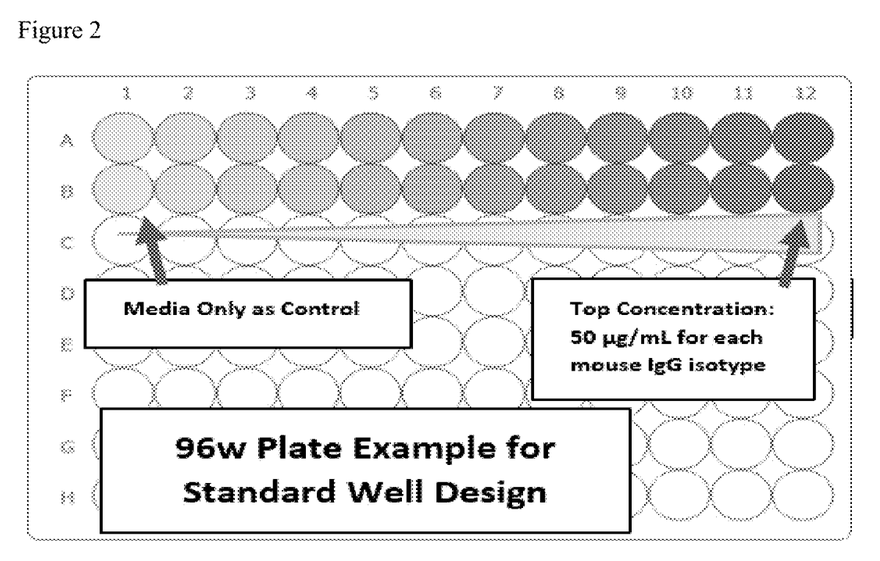
FIG. 2 is a diagram of an exemplary setup of standard wells in the microtiter plate.

FIG. 2 shows an exemplary setup of standard wells in the microtiter plate. Here an exemplary design of the IgG Standard wells in 96-well microtiter plate is shown. Each specific well has 4 isotype proteins with the same amount of each mouse IgG isotype (mouse IgG1, 2a, 2b, and 3). Top concentration wells (duplicate wells) on the right (A12 and B12) have the highest concentration 50 ug/mL for each isotype. 1:2 serial titration was applied from the right to the left. For example, Well A11 and B11 will have 25 ug/mL for each isotype. Well A1 and B1 are used as negative control with fresh/blank media but without any mouse IgG protein standard. A user has the flexibility to determine the new top concentration or dilution factor or how many dilution steps. For example, a user can use 100 ug/mL per isotype for the top concentration, and use 1:3 serial titration, and use 6 dilution steps rather than 11 dilution steps as shown in the standard design in FIG. 2. A user can use the same standard design on other plate types such as 384-well plate. For the same plate without standards, for example, row C-H in FIG. 2, a user can run the unknown mouse IgG samples with or without cells.

In one exemplary technique, cells and beads can be detected via separation in 2D scatter plots, based on size (Forward scatter, FSC) and/or granularity (Side scatter, SSC). Singlet beads but not doublet beads can be gated by using a 2D plot (FSC-Height vs. FSC-Area). Singlet beads will be the right population at the 45 degrees in 2D plot (FSC-Height vs. FSC-Area). Doublet or aggregates will be on the left. Singlet beads can be further separated into 4 capture bead population in a 2D plot (red fluorescence channel RL1-Height vs. FSC-Height). Live cells can be gated from all cells in 1D histogram of red fluorescence channel RL1-Height. The live cells will be the left populations with less fluorescent staining. Dead or dying cells will pick up more dye and will be the right cell population (not gated).

For 4 mouse IgG isotypes, 1 standard curve may be generated per isotype per protocol. The detection dynamic range and the linear detection range are summarized in Table 1. Duplicate wells were run for each tested concentration. Use of FORECYT™ software (Intellicyt) generates the standard curves automatically with each point representing the mean +/−standard deviation. The detection dynamic range and the linear detection range are shown in Table 1 (mIgG1 is mouse IgG1, mIgG2a is mouse IgG2a etc.).

For curve fitting: FORECYT™ software (Intellicyt) with a 4PL fitting method with 1/Y square for fit weight was used, which automatically detected the linear range and provided the linear range. The linear range is that range of input or output values for which an electronic amplifier produced an output signal that was a direct, linear function of the input signal. That is, the output can be represented by the equation: Output=Input×Gain. The linear range provides a precise/sensitive quantitation when the signal of unknown samples falls into this range.

The detection range used means the range between the low-end detection limit (minimal concentration with the signal that is 3 * standard deviation of the blank with 0 μg/mL IgG, and the high-end detection limit (maximal concentration with the signal that is 3* standard deviation of the saturation signal determined by FORECYT™ software). If the standard curve does not reach saturation, the highest tested concentration (here is 100 μg/mL) is used.

For samples from hybridoma culture, full competition protocol may be recommended; for samples from mouse B cell culture, pre-incubation protocol may be recommended.

Example 2

Below are described exemplary protocols of the assays of certain aspects, to identify cells that produce high levels of a secreted protein or IgG antibody.
1. Candidate producer cells are diluted and distributed in wells of a multiwell "microtiter" plate so that only one cell is deposited in each well. The methods for doing this are well described in the art. One cell per well is practically a difficult goal to achieve; although most wells contain one cell, there are many wells which have zero cells, and many wells which contain multiple cells. In general it is necessary to screen hundreds of thousands of wells to find a small number of cell lines that secrete high levels of protein.
2. The cells are allowed to proliferate to increase the numbers of cells in each well. Because proliferation is occurring through mitosis, the daughter cells in each well will be exact copies of the original cell(s) that was (were) deposited in the well.
3. As the cells proliferate, they produce the protein biologic (i.e., IgG antibody) and secrete it into the culture supernatant.

TABLE 1

Detection Dynamic Range and Linear Detection Range

| Protocol | Range | mIgG1 | mIgG2a | mIgG2b | mIgG3 |
| --- | --- | --- | --- | --- | --- |
| Full Competition Protocol (For Hybridoma culture: 1-50 ug/mL IgG) | Detection Dynamic Range | 0.05-100 ug/mL | 0.8-100 ugmL | 0.025-100 ug/mL | 0.025-100 ugmL |
| | Linear Range | 0.9-100 ug/mL | 0.8-49 ug/mL | 0.4-14 ug/mL | 0.8-87 ug/mL |
| Pre-incubation Protocol (For B Cells Sample: 0.1-2 ug/mL IgG) | Detection Dynamic Range | 0.006-100 ug/mL | 0.006-25 ug/mL | 0.01-12.5 ug/mL | 0.01-100 ug/mL |
| | Linear Range | 0.1-4.6 ug/mL | 0.2-3 ug/mL | 0.07-1 ug/mL | 0.5-59 ug/mL |

The top concentration tested in the standard curve was 100 μg/mL per isotype. Higher than 100 μg/mL was not tested in the assay. Standards were diluted in DMEM culture media with 10% fetal bovine serum. 19-point 1:2 serial titration was run in the test.

4. An undiluted aliquot of each well, containing a representative amount of secreted protein and producer cells is transferred to a new well in a lyophilized assay plate. Each well of the lyophilized assay plate contains lyophilized reagents that are used to quantitate the amount of secreted protein present and, simultaneously can be used to assay the number of producer cells present in the sample. Quantitation reagents prepared in non-lyophilized form from a reagent kit could also be used for the analysis. The lyophilized assay plates or the reagent kit contains can the following items:
  a. A capture bead—for example, fluorescent microspheres coated with a molecule which binds to a specific site on the secreted protein and captures the secreted proteins onto the surface of the microspheres.
  b. Detection molecules which are labeled with a fluorescent probe and which bind to a different region on the secreted protein which has been captured onto the microsphere surface. The intensity of the fluorescence associated with each microsphere is then directly correlated to the number of secreted, captured protein molecules present in the sample.
5. After an incubation time, the samples are analyzed by high throughput flow cytometry. One example of a high throughput flow cytometry system is the HyperCyt™ HTFC system in combination with a flow cytometer which can analyze of thousands of samples in minutes.
6. The high throughput flow cytometry detection system is set up to report the fluorescent intensity of the bead-associated detection molecule, which is used to calculate the secreted protein concentration from a standard curve. In addition, the number of producer cells present in the sample can be determined simultaneously. A proprietary software analysis package automatically determines the ratio of secreted protein to cell number, and calculates the secreted protein concentration on a per cell basis. If the high throughput flow cytometry system is used in conjunction with a cell sorter, the software also controls the system to sort individual cells from high secretor wells to further purify a desired cell line.

$1^{st}$ Protocol—IgG Quant Assay-Stepwise Protocol (Exemplary):
1. Vortex the protein G-coated beads (6-8 um size, 0.5% v/v). Do 1:15 dilution of beads in 0.1% bovine serum albumin (BSA) in phosphate buffer saline (PBS). Mix the diluted beads, and add 5 uL/well beads into each well of a micro-titer assay plate (either 96-well plate or 384-well plate);
2. In each well of the assay plate, add 20 uL IgG sample (either IgG standard to generate IgG standard curve or suspension CHO cell culture/secreted IgG mixture or just the IgG supernatant from the suspension CHO cell culture).
3. Briefly spin the assay plate to bring down the sample to the well bottom (500 g×8 seconds). Mix samples in the plate on a plate shaker (2000 rpm×20 seconds).
4. Incubate the assay plate at room temperature for 30 minutes. Protect the plate from light.
5. Prepare the combined detection reagent: make 20 ug/mL FITC-Fc fragment (Jackson ImmunoResearch Laboratory Inc.) and 20 nM FL4 membrane integrity dye (IntelliCyt Corporation) in 0.1% BSA in PBS in the same tube.
6. Add 5 uL combined detection reagent in each well of the assay plate.
7. Briefly spin the assay plate to bring down the sample to the well bottom (500 g×8 seconds). Mix samples in the plate on a plate shaker (2000 rpm×20 seconds).
8. Incubate the assay plate at room temperature for 30 minutes. Protect the plate from light.
9. Acquire the samples from the assay plate by high throughput flow cytometer such as IntelliCyt IQUE™ Screener platform.

Example 2

$2^{nd}$ Protocol—IgG Quant Assay-Simultaneous Protocol:
1. Prepare the combined detection reagent: make 20 ug/mL FITC-Fc fragment (Jackson ImmunoResearch Laboratory Inc.) and 20 nM FL4 membrane integrity dye (IntelliCyt Corporation) in 0.1% BSA in PBS in the same tube.
2. Add 5 uL combined detection reagent in each well of a microtiter assay plate (either 96-well plate or 384-well plate).
3. In each well of the assay plate, add 20 uL IgG sample (either IgG standard to generate IgG standard curve or suspension CHO cell culture/secreted IgG mixture or just the IgG supernatant from the suspension CHO cell culture).
4. Briefly spin the assay plate to bring down the sample and the combined detection reagent mixture to the well bottom (500 g×8 seconds). Mix samples in the plate on a plate shaker (2000 rpm×20 seconds).
5. Vortex the protein G-coated beads (6-8 um size, 0.5% v/v). Do 1:15 dilution of beads in 0.1% bovine serum albumin (BSA) in phosphate buffer saline (PBS). Mix the diluted beads, and add 5 uL/well beads into each well of the assay plate with the sample/detection mixture.
6. Briefly spin the assay plate to bring down the liquid to the well bottom (500 g×8 seconds). Mix samples in the plate on a plate shaker (2000 rpm×20 seconds).
7. Incubate the assay plate at room temperature for 60 minutes. Protect the plate from light.
8. Acquire the samples from the assay plate by high throughput flow cytometer such as IntelliCyt IQUE™ Screener platform.

$3^{rd}$ Protocol—IgG Quant & Light Chain Detection Assay-Stepwise Protocol (Exemplary):
1. Vortex the protein G-coated beads (6-8 um size, 0.5% v/v). Do 1:15 dilution of beads in 0.1% bovine serum albumin (BSA) in phosphate buffer saline (PBS). Mix the diluted beads, and add 5 uL/well beads into each well of a micro-titer assay plate (either 96-well plate or 384-well plate);
2. In each well of the assay plate, add 20 uL IgG sample (either IgG standard to generate IgG standard curve or suspension CHO cell culture/secreted IgG mixture or just the IgG supernatant from the suspension CHO cell culture).
3. Briefly spin the assay plate to bring down the sample to the well bottom (500 g×8 seconds). Mix samples in the plate on a plate shaker (2000 rpm×20 seconds).
4. Incubate the assay plate at room temperature for 30 minutes. Protect the plate from light.
5. Prepare the combined detection reagent: make 20 ug/mL FITC-Fc fragment (Jackson ImmunoResearch Laboratory Inc.), and 10 ug/mL PE-F(ab')2 anti-human Ig kappa light chain (ThermoFisher), and 20 nM FL4 membrane integrity dye (IntelliCyt Corporation) in 0.1% BSA in PBS in the same tube.
6. Add 5 uL combined detection reagent in each well of the assay plate.
7. Briefly spin the assay plate to bring down the sample to the well bottom (500 g×8 seconds). Mix samples in the plate on a plate shaker (2000 rpm×20 seconds).
8. Incubate the assay plate at room temperature for 30 minutes. Protect the plate from light.
9. Acquire the samples from the assay plate by high throughput flow cytometer such as IntelliCyt IQUE™ Screener platform.

Example 4

4th Protocol—IgG Quant and Light Chain Detection Assay-Simultaneous Protocol:
1. Prepare the combined detection reagent: make 20 ug/mL FITC-Fc fragment (Jackson ImmunoResearch Laboratory Inc.), and 10 ug/mL PE-F(ab')2 anti-human Ig kappa light chain (ThermoFisher), and 20 nM FL4 membrane integrity dye (IntelliCyt Corporation) in 0.1% BSA in PBS in the same tube.
2. Add 5 uL combined detection reagent in each well of a microtiter assay plate (either 96-well plate or 384-well plate).
3. In each well of the assay plate, add 20 uL IgG sample (either IgG standard to generate IgG standard curve or suspension CHO cell culture/secreted IgG mixture or just the IgG supernatant from the suspension CHO cell culture).
4. Briefly spin the assay plate to bring down the sample and the combined detection reagent mixture to the well bottom (500 g×8 seconds). Mix samples in the plate on a plate shaker (2000 rpm×20 seconds).
5. Vortex the protein G-coated beads (6-8 um size, 0.5% v/v.). Do 1:15 dilution of beads in 0.1% bovine serum albumin (BSA) in phosphate buffer saline (PBS). Mix the diluted beads, and add 5 uL/well beads into each well of the assay plate with the sample/detection mixture.
6. Briefly spin the assay plate to bring down the liquid to the well bottom (500 g×8 seconds). Mix samples in the plate on a plate shaker (2000 rpm×20 seconds).
7. Incubate the assay plate at room temperature for 60 minutes. Protect the plate from light.
8. Acquire the samples from the assay plate by high throughput flow cytometer such as IntelliCyt IQUE™ Screener platform.

We claim:

1. A method for determining immunoglobulin gamma (IgG) antibody isotype concentration from a biological sample, comprising:
   (a) incubating in a microtiter plate well:
      (i) an undiluted biological sample comprising (A) B cells or cell hybridoma supernatant with or without cells; and (B) IgG antibodies;
      (ii) a detection reagent comprising a defined concentration ratio of three or more different target IgG protein isotypes, or fragments thereof, wherein the three or more different target IgG protein isotypes, or fragments thereof, are detectably labeled; and
      (iii) three or more different bead-bound IgG isotype-specific populations of capture reagent in a single reaction mixture, wherein each bead-bound IgG isotype-specific population of capture reagent is separately distinguishable and comprises binding molecules that selectively bind to specific IgG antibody isotypes,
      wherein the incubating promotes binding of the three or more different target IgG protein isotypes, or fragments thereof, and any of the IgG antibodies present in the biological sample to the bead-bound IgG isotype-specific population of capture reagents to produce bead-bound IgG isotype-specific binding complexes in the single reaction mixture; and
   (b) detecting in a flow cytometer signal from the bead-bound IgG isotype-specific binding complexes in the single reaction mixture to determine a concentration for any of the IgG antibodies present in the biological sample, wherein the amount of an IgG antibody isotype protein present in the biological sample is inversely proportional to each detected signal from the relevant bead-bound IgG isotype-specific binding complex;
   wherein the method is performed without wash steps, and quantifies a range from 1 μg/mL to 50 μg/mL when step (a) comprises incubating the sample with the detection reagent (ii) to form an IgG antibody-target IgG protein mixture in the well followed by incubation with the three or more different bead-bound IgG isotype-specific populations of the capture reagent (iii) in the single reaction mixture and quantifies a range from 0.1 μg/mL to 2 μg/mL for any of the IgG antibodies present in the biological sample when step (a) comprises first incubating the sample with the three or more different bead-bound IgG isotype-specific populations of capture reagent (iii) to produce an IgG antibody-IgG isotype-specific capture reagent complex in the well for each of the three or more different bead-bound IgG isotype-specific populations present in the well, and then incubating the IgG antibody-IgG isotype-specific capture reagent complex with the detection reagent (ii) to produce the detectably labeled bead-bound IgG isotype-specific binding complexes in the single reaction mixture.

2. The method of claim 1, further comprising
   (c) incubating serial dilutions of a control sample, wherein each dilution of the serial dilutions of the control sample is present in a separate well of a microtiter plate, with the detection reagent to generate control mixtures, wherein the control sample comprises three or more different unlabeled IgG protein isotypes, or fragments thereof, that correspond to the three or more different target IgG protein isotypes, or fragments thereof, in the detection reagent, wherein the incubation promotes mixing of the three or more different unlabeled IgG protein isotypes in the control sample and the three or more different target IgG protein isotypes, or fragments thereof;
   (d) incubating the control mixtures with the three or more different bead-bound IgG isotype-specific populations of capture reagent, wherein the incubating promotes competitive binding of the three or more different target IgG protein isotypes, or fragments thereof, and the three or more different unlabeled IgG protein isotypes, or fragments thereof, to the three or more different bead-bound IgG isotype-specific population of capture reagent, to produce control IgG isotype-specific binding complexes; and
   (e) generating a standard curve for each IgG protein isotype by analysis of the signal from the IgG isotype-specific binding complexes, wherein the concentration of any of the IgG antibodies in the biological sample is measured by reference to the standard curve for each IgG protein isotype.

3. The method of claim 1, wherein the detection reagent comprises a defined concentration ratio of four or more different target IgG protein isotypes, or fragments thereof, wherein the four or more different target IgG protein isotypes, or fragments thereof, are detectably labeled, and wherein the concentration of four or more IgG antibody isotypes is determined in each biological sample.

4. The method of claim 1, wherein the undiluted biological sample comprises cells and the detection reagent further comprises a detectable cell viability marker, and wherein the method further comprises measuring cell viability and/or cell number in the biological sample in the flow cytometer.

5. The method of claim 1, wherein the binding molecules comprise antibodies, affimers, aptamers, and/or Fc receptors.

6. The method of claim 1, wherein the method further comprises determining the total IgG antibody concentration in the biological sample.

7. The method of claim 1, wherein the biological sample comprises a cell sample.

8. The method of claim 1, wherein the biological sample comprises mouse B cells or mouse cell hybridoma supernatant with or without cells, wherein the different IgG isotypes are selected from the group consisting of mouse IgG1, IgG2a, IgG2b, and IgG3.

9. The method of claim 1, wherein the biological sample comprises human cells, wherein the different IgG isotypes are selected from the group consisting of human IgG1, IgG2, IgG3, and IgG4.

10. The method of claim 1, wherein the biological sample comprises rat cells, wherein the different IgG isotypes are selected from the group consisting of rat IgG1, IgG2a, IgG2b, IgG2c.

11. The method of claim 1, wherein the biological sample comprises:
 rabbit cells or sheep cells, wherein the different IgG isotypes are selected from the group consisting of rabbit or sheep IgG;
 (ii) goat cells, pig cells, or bovine cells, wherein the different IgG isotypes are selected from the group consisting of goat, pig, or bovine IgG1 and IgG2;
 (iii) horse cells, wherein the different IgG isotypes are selected from the group consisting of horse IgGa, IgGb, IgGt; or
 (iv) monkey cells, wherein the different IgG isotypes are selected from the group consisting of monkey IgG1, IgG2, IgG3, IgG4.

* * * * *